(12) United States Patent
Choi et al.

(10) Patent No.: US 12,246,144 B2
(45) Date of Patent: Mar. 11, 2025

(54) GUIDEWIRE STEERING MICRO-ROBOT

(71) Applicant: Daegu Gyeongbuk Institute of Science and Technology, Hyeonpung-myeon (KR)

(72) Inventors: Hong Soo Choi, Daegu (KR); Jun Sun Hwang, Gyeonggi-do (KR); Jin Young Kim, Daegu (KR); Beom Joo Kim, Daegu (KR); Hyunki Lee, Daegu (KR); Sung Jun Lim, Daegu (KR); Hwajun Jeong, Incheon (KR)

(73) Assignee: Daegu Gyeongbuk Institute of Science and Technology (KR)

( * ) Notice: Subject to any disclaimer, the term of this patent is extended or adjusted under 35 U.S.C. 154(b) by 385 days.

(21) Appl. No.: 17/499,638

(22) Filed: Oct. 12, 2021

(65) Prior Publication Data

US 2022/0160999 A1    May 26, 2022

(30) Foreign Application Priority Data

Nov. 20, 2020   (KR) .................. 10-2020-0156778

(51) Int. Cl.
*A61M 25/01*   (2006.01)

(52) U.S. Cl.
CPC .... *A61M 25/0158* (2013.01); *A61M 25/0138* (2013.01); *A61M 2205/583* (2013.01)

(58) Field of Classification Search
CPC ............ A61M 25/09; A61M 25/09041; A61M 25/0158; A61M 25/0127; A61M 2025/0166; A61M 2205/0272; A61B 5/6851; A61B 2017/00318
See application file for complete search history.

(56) References Cited

U.S. PATENT DOCUMENTS

| | | | |
|---|---|---|---|
| 10,682,051 B2* | 6/2020 | Matz | ........................ A61B 3/13 |
| 2016/0256120 A1 | 9/2016 | Stone et al. | |
| 2019/0192814 A1 | 6/2019 | Tang et al. | |
| 2019/0231269 A1 | 8/2019 | Cao | |
| 2020/0072980 A1* | 3/2020 | Lee | ........................ A61K 41/00 |
| 2020/0330730 A1* | 10/2020 | Creighton | ............... A61L 29/18 |

OTHER PUBLICATIONS

Kim, Y. et al.; "Ferromagnetic soft continuum robots"; Science Robotics, vol. 4, eaax7329; Aug. 28, 2019; 32 pages.
Azizi, A. et al.; "Using the Fringe Field of a Clinical MRI Scanner Enables Robotic Navigation of Tethered Instruments in Deeper Vascular Regions"; Science Robotics, vol. 4, eaax7342; Nov. 27, 2019; 13 pages.

* cited by examiner

*Primary Examiner* — Chelsea E Stinson
*Assistant Examiner* — Anh Bui

(57) ABSTRACT

Disclosed is a guidewire steering micro-robot. The guidewire steering micro-robot includes a guidewire, and a steering unit provided at an end portion of the guidewire, the steering unit including a magnetic body to control and steer a position of the guidewire by an external magnetic field.

15 Claims, 6 Drawing Sheets

GUIDEWIRE STEERING MICRO-ROBOT

CROSS-REFERENCE TO RELATED APPLICATION

This application claims the benefit of Korean Patent Application No. 10-2020-0156778 filed on Nov. 20, 2020, in the Korean Intellectual Property Office, the entire disclosure of which is incorporated herein by reference for all purposes.

BACKGROUND

1. Field of the Invention

One or more example embodiments relate to a guidewire steering micro-robot.

2. Description of the Related Art

Vascular intervention is a method of treating a vascular disease through a blood vessel rather than a surgery. Vascular intervention is performed by inserting a small guidewire into a blood vessel and moving the guidewire to a target site of a disease along a blood vessel. Due to an absence of a nerve that allows the feeling of sensation or pain in a blood vessel, a patient may feel no to little discomfort.

Vascular intervention requires to send a guidewire to a target point of disease outbreak without damaging a blood vessel. Thus, it requires a high degree of skills and professionalism. Conventionally, an X-ray device was used to track a position of a guidewire inserted into a blood vessel. However, since a patient may be continuously exposed to an X-ray for a position tracking, it may cause various damages to a body and a gene such as cataracts and skin cancer. In addition, an operator who frequently performs an X-ray procedure is exposed to radiation for a long time, and thus, may have a serious radiation exposure side effect. Furthermore, when using an X-ray, a vascular contrast medium is injected together. However, it has a risk of causing a serious side effect including a shock, a cardiac insufficiency, and a cardiac arrest due to a patient's diathesis.

The above description is information the inventor(s) acquired during the course of conceiving the present disclosure, or already possessed at the time, and is not necessarily art publicly known before the present application was filed.

SUMMARY

Example embodiments provide a guidewire steering micro-robot capable of confirming a position of a guidewire inserted into a body without using radiation during a vascular intervention procedure.

The technical tasks obtainable from the present disclosure are non-limited by the above-mentioned technical tasks. And, other unmentioned technical tasks can be clearly understood from the following description by those having ordinary skill in the technical field to which the present disclosure pertains.

According to an aspect, there is provided a guidewire steering micro-robot.

The guidewire steering micro-robot includes a guidewire, and a steering unit provided at an end portion of the guidewire, the steering unit including a magnetic body to control and steer a position of the guidewire by an external magnetic field.

The steering unit may further include a connector connecting the guidewire and the steering unit.

The steering unit may further include a position display unit configured to absorb and emit a light irradiated from an outside.

The position display unit may include a micro nanoparticle to absorb and re-emit a body transmittable light energy and a shell enclosing the micro nanoparticle.

The light energy may be a light energy within a shortwave infrared band.

The connector may be connected to the guidewire and the steering unit by heat or an adhesive.

The guidewire and the steering unit may be inserted into the connector.

The guidewire steering micro-robot may further include a flexible polymer between the guidewire and the steering unit.

The connector may include a hollow inside and have a shape of a coil for allowing the guidewire and the steering unit to be inserted into the connector.

The coil may be formed of a biocompatible metal or a polymer material.

The connector may further include a spring.

The magnetic body may include a hollow, and the end portion of the guidewire may be inserted into and connected to the hollow of the magnetic body.

The guidewire steering micro-robot may further include a tip configured to fix a position of the magnetic body.

The tip may be formed of a metal or a polymer.

Additional aspects of example embodiments will be set forth in part in the description which follows and, in part, will be apparent from the description, or may be learned by practice of the disclosure.

According to example embodiments, a guidewire steering micro-robot may confirm a position of a guidewire inserted into the body without using radiation during vascular intervention procedure.

The effects of the guidewire steering micro-robot are not limited to the above-mentioned effects. And, other unmentioned effects can be clearly understood from the above description by those having ordinary skill in the technical field to which the present disclosure pertains.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

Figure 1:
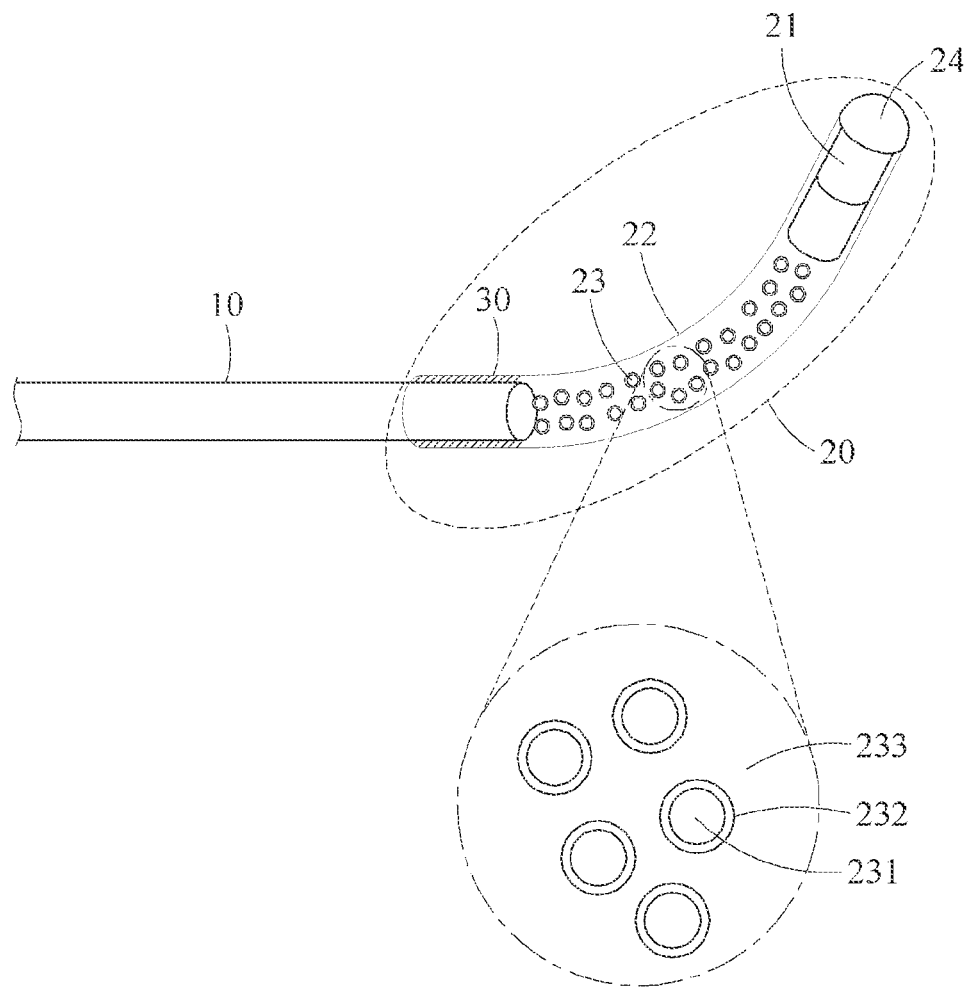
FIG. 1 illustrates a configuration of a guidewire steering micro-robot according to an example embodiment.

The accompanying drawings illustrate preferred embodiments of the present invention, and are provided together with the detailed description for better understanding of the technical idea of the present invention. Therefore, the present invention should not be construed as being limited to the embodiments set forth in the drawings.

DETAILED DESCRIPTION

Hereinafter, example embodiments will be described in detail with reference to the accompanying drawings. However, various alterations and modifications may be made to the example embodiments. Here, the example embodiments are not construed as limited to the disclosure. The example embodiments should be understood to include all changes, equivalents, and replacements within the idea and the technical scope of the disclosure.

The terminology used herein is for the purpose of describing particular example embodiments only and is not to be limiting of the example embodiments. The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the example embodiments with reference to the accompanying drawings, like reference numerals refer to like constituent elements and a repeated description related thereto will be omitted. In the description of example embodiments, detailed description of well-known related structures or functions will be omitted when it is deemed that such description will cause ambiguous interpretation of the present disclosure.

Also, in the description of the components, terms such as first, second, A, B, (a), (b) or the like may be used herein when describing components of the present disclosure. These terms are used only for the purpose of discriminating one constituent element from another constituent element, and the nature, the sequences, or the orders of the constituent elements are not limited by the terms. When one constituent element is described as being "connected", "coupled", or "attached" to another constituent element, it should be understood that one constituent element can be connected or attached directly to another constituent element, and an intervening constituent element can also be "connected", "coupled", or "attached" to the constituent elements.

The constituent element, which has the same common function as the constituent element included in any one embodiment, will be described by using the same name in other embodiments. Unless disclosed to the contrary, the configuration disclosed in any one embodiment may be applied to other embodiments, and the specific description of the repeated configuration will be omitted.

Figure 2:
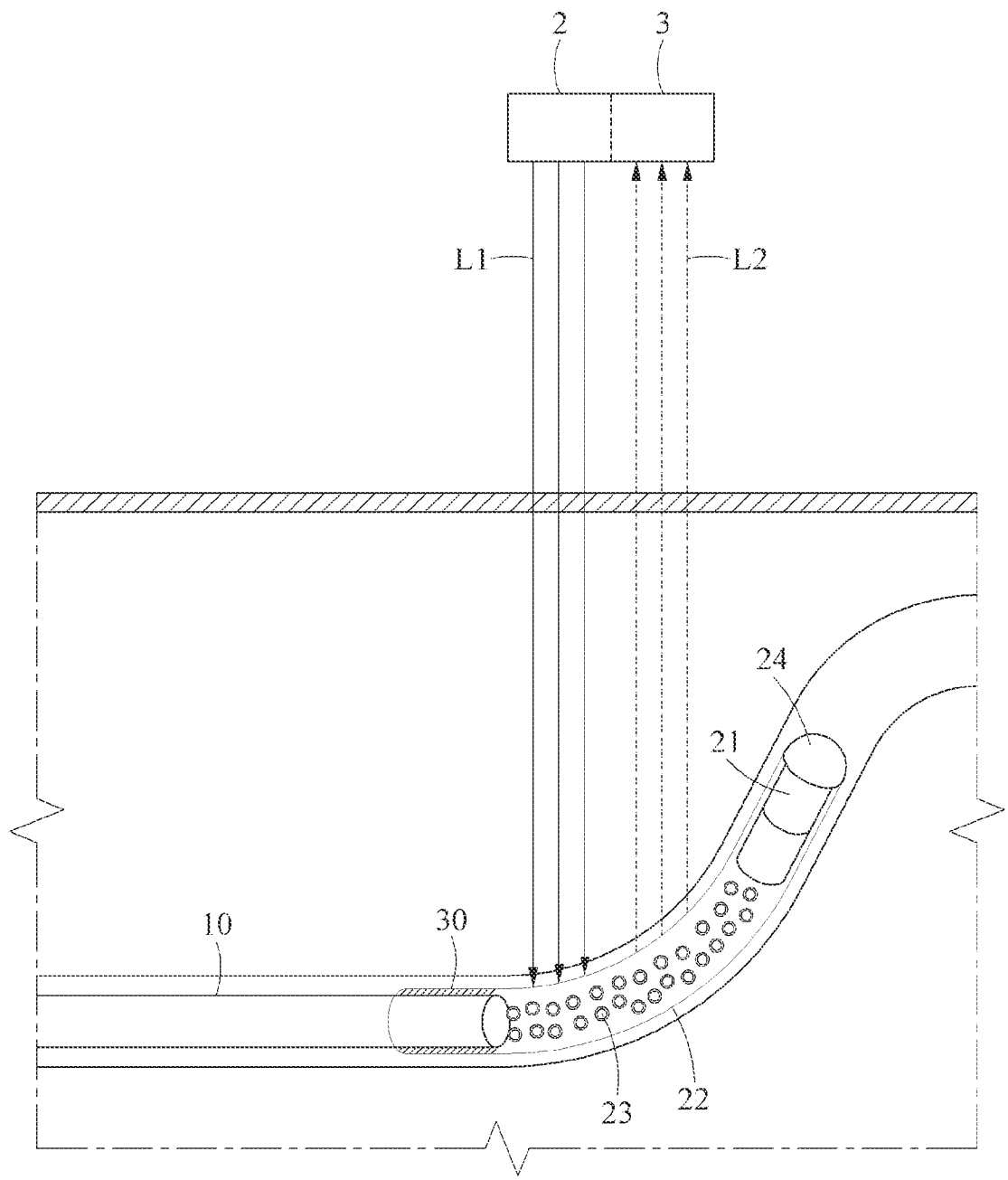
FIG. 2 illustrates a concept of confirming a position of a guidewire steering micro-robot according to an example embodiment.
Figure 3:
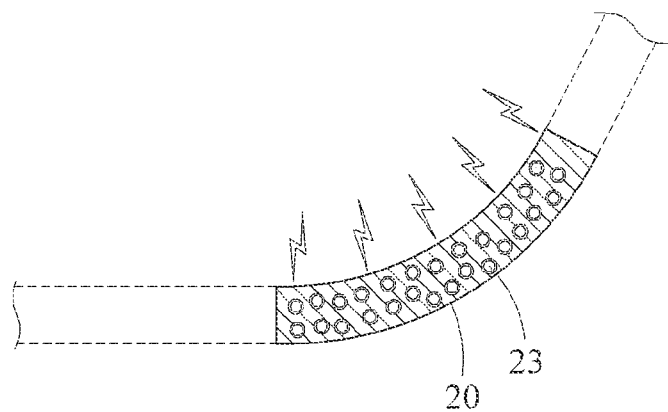
FIG. 3 illustrates an image of a guidewire steering micro-robot confirmed by a shortwave infrared according to an example embodiment.

With reference to the drawings, a guidewire steering micro-robot 1 will be described. For reference, FIG. 1 illustrates a configuration of the guidewire steering micro-robot 1 according to an example embodiment, FIG. 2 illustrates a concept of confirming a position of the guidewire steering micro-robot 1 according to an example embodiment, and FIG. 3 is an image of the guidewire steering micro-robot 1 confirmed by a shortwave infrared according to an example embodiment.

When the guidewire steering micro-robot 1 is inserted into a body, the position of the guidewire steering micro-robot 1 may be identified without using radiation, and a position of a guidewire 10 may be controlled by using an external magnetic field.

Referring to FIG. 1, the guidewire steering micro-robot 1 may include the guidewire 10 and a steering unit 20.

The guidewire 10 may be inserted into an inside of a catheter to move an angiographic catheter or a cardiac catheter to a target blood vessel, and for example, may be formed of a steel wire. In addition, the guidewire 10 may be formed of a flexible metal or a synthetic resin.

An external diameter of the guidewire 10 may be shaped in a size that may pass through a blood vessel of a patient, and may be identical to or slightly smaller than an internal diameter of a connector 22 of the steering unit 20, which will be described below.

The guidewire 10 may further include a controller (not shown) to control a movement of the guidewire 10 from an outside or remotely and a catheter controller (not shown) to transfer a catheter (not shown) to a target point such as a site of angiostenosis or occlusion along the inserted guidewire 10.

The guidewire 10 and the steering unit 20 may be connected and coupled by a junction 30. The junction 30 may be interposed between the connector 22 of the steering unit 20 and the guidewire 10. The junction 30 may connect the guidewire 10 and the steering unit 20 to the connector 22 by heat or an adhesive. Alternatively, the steering unit 20 and the connector 22 may be coupled by an interference fit method without the junction 30.

The steering unit 20 may include a magnetic body 21, the connector 22 connecting the guidewire 10 and the magnetic body 21, and a position display unit 23 provided at the connector 22 and configured to absorb and emit a light irradiated from an outside.

The magnetic body 21 may be provided at an end portion of the steering unit 20. The magnetic body 21 may be provided in a shape inserted into the connector 22, which will be described below.

The magnetic body 21 may control a position of the steering unit 20 and a position of the guidewire 10 connected to the steering unit 20 in response to an external magnetic field generated by a magnetic field controller which is placed outside a patient.

Here, the magnetic body 21 may include a magnetic material which is not highly corrosive to have a predetermined degree of magnetism.

For example, the magnetic body 21 may be a magnetic body including any one or any combination of iron oxides ($Fe_2O_3$ and $Fe_2O_4$), nickel (Ni), cobalt (Co), and neodymium (Nd), but is not limited thereto.

The connector 22 is formed in a shape of a tube for accommodating the magnetic body 21 therein. Here, the connector 22 may be formed of a flexible material that can be bent. The connector 22 may accurately steer a direction of the guidewire 10 to a target point by bending flexibly when the magnetic body 21 moves through a blood vessel in response to an external magnetic field. In addition, the connector 22 may further include a biocompatible material, and thus, may prevent a potential side effect during a procedure.

For example, the connector 22 may include any one or any combination of silicone, gore-tex, natural rubber, polymethyl methacrylate (PMMA), polyhydroxyethylmethacrylate (PHEMA), and polyethylene terephthalate (PET).

If the connector 22 is too thick, it may act as a resistive element that reduces the degree of bending of the steering unit 20 and may also act as an element that increases a stiffness of the steering unit 20. Thus, a width of the connector 22 may be selected in an appropriate thickness so that the steering unit 20 may have an appropriate stiffness and flexibility.

The position display unit 23 may be provided at the connector 22, between the guidewire 10 and the magnetic body 21. The position display unit 23 may be formed of a plurality of micro nanoparticles 231, a shell 232 enclosing a surface of each of the micro nanoparticles 231, and a matrix 233.

The micro nanoparticles 231 may be formed of various types of particles, such as quantum dots and magnetic particles. Alternatively, the micro nanoparticles 231 may be particles in which quantum dots and magnetic particles are mixed in a predetermined proportion.

The shell 232 may be formed of an additional material different from that of a micro nanoparticle 231 and may enclose a surface of the micro nanoparticle 231. The shell 232 may be formed of a magnetic material or an inorganic material.

The micro nanoparticle 231 and the shell 232 may have a core-shell structure. The shell 232 may form a protective layer to protect the micro nanoparticle 231 and allow the micro nanoparticle 231 to have high luminous efficiency and stability.

Here, when the micro nanoparticle 231 includes a quantum dot, the micro nanoparticle 231 may absorb and re-emit a body transmittable light energy, allowing the detection of the positions of the guidewire 10 and the steering unit 20 located inside a body from the outside. Here, as the body transmittable light energy, a light energy which is harmless to an inside of a body such as a light within a shortwave infrared band may be used.

The micro nanoparticle 231 may emit a light with a predetermined frequency in accordance with a size, a shape, and a material of a particle when receiving a light energy. A position of the micro nanoparticle 231 as well as a position of the guidewire 10 inside of a body may be identified by sensing the emitted light.

In addition, the micro nanoparticle 231 may efficiently change a frequency and a wavelength of light absorption or emission by adjusting a size of a particle only. Thus, an intensity of light emission may be controllable in accordance with a body injection circumstance.

The matrix 233 may be a key substance forming the connector 22. The matrix 233 may uniformly dispersively accommodate the micro nanoparticles 231. For example, the matrix 233 may be a biocompatible polymer.

A tip 24 may be provided at an end portion of the magnetic body 21. The tip 24 may fix a position of the magnetic body 21 and prevent the magnetic body 21 from escaping to an outside. The tip 24 may be formed of a polymer material or a metal.

Referring to FIGS. 2 and 3, if a light irradiator 2 irradiates a first light (L1) to a patient, the micro nanoparticle 231 of the position display unit 23 of the steering unit 20 may absorb the first light (L1) and emit a second light (L2). For example, as the light irradiator 2, any types of source apparatuses capable of generating the first light (L1) may be applied. The light irradiator 2 may include a light-emitting diode capable of irradiating a light within a predetermined wavelength band or a laser. The first light (L1) may be a light with a near-infrared region wavelength (that is, approximately 750 nanometers (nm) or 1 micrometer (μm) of an electromagnetic spectrum with a high body transmittance, or a light with a wavelength within a shortwave infrared region (that is, approximately 1 μm or 2.5 μm).

In addition, a light detector 3 may detect the second light (L2) emitted from the micro nanoparticle 231 of the position display unit 23 of the steering unit 20. For example, the light detector 3 may be a shortwave infrared camera capable of detecting a light within a shortwave infrared wavelength band emitted from the micro nanoparticle 231.

Referring to FIG. 3, if a light within a shortwave infrared band is irradiated to the guidewire steering micro-robot 1 inserted into a body, the micro nanoparticle 231 may re-emit the light. Referring to FIG. 3, since the steering unit 20 with the micro nanoparticle 231 is clearly detected, a position and a bending of the steering unit 20 may be easily confirmed. Furthermore, since parts without the micro nanoparticles 231 are not detected on the screen, a position of the steering unit 20 is easily confirmed, and is not confused with the guidewire 10 and surrounding tissues.

Figure 4:
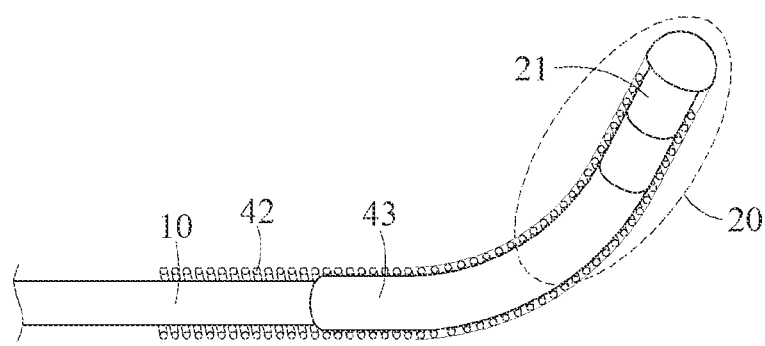
FIG. 4 illustrates a configuration of a guidewire steering micro-robot according to a second example embodiment.
Figure 5:
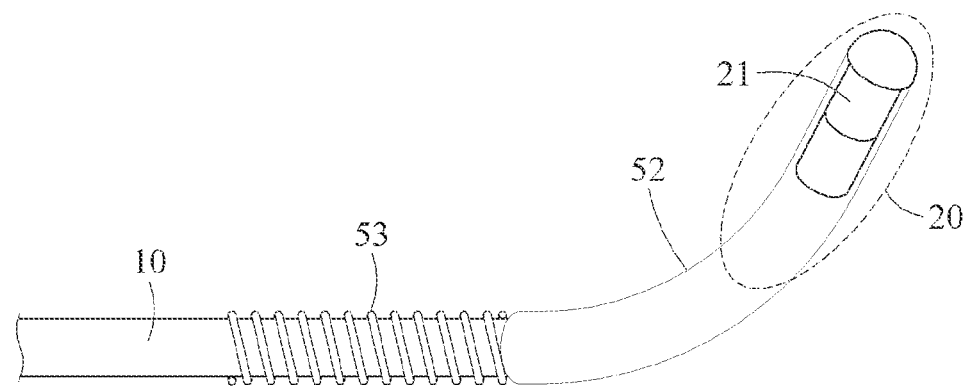
FIG. 5 illustrates a configuration of a guidewire steering micro-robot according to a third example embodiment.
Figure 6:
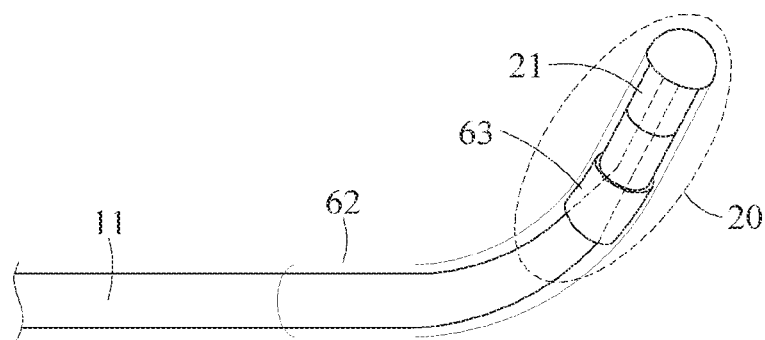
FIG. 6 illustrates a configuration of a guidewire steering micro-robot according to a fourth example embodiment.

Meanwhile, FIGS. 4 to 6 illustrate modified example embodiments of the guidewire steering micro-robot 1, described above. For reference, FIG. 4 illustrates a configuration of a guidewire steering micro-robot 4 according to a second example embodiment, FIG. 5 illustrates a configuration of a guidewire steering micro-robot 5 according to a third example embodiment, and FIG. 6 illustrates a configuration of a guidewire steering micro-robot 6 according to a fourth example embodiment. In addition, the guidewire steering micro-robots 4, 5, and 6 which will be described below may be substantially the same as the guidewire steering micro-robot 1 described above, except for a configuration of the connector 22. Thus, like reference numerals and names are used for like constituent elements, and a duplicated description will be omitted herein.

Referring to FIG. 4, a connector 42 of the guidewire steering micro-robot 4 may include have a shape of a coil including a hollow inside, and allow the guidewire 10 and the steering unit 20 to be inserted into the connector 42.

The connector 42 may be formed of a biocompatible metal or a polymer material. For example, the connector 42 may be formed of platinum, gold, or urethane.

A flexible polymer 43 may be provided between the guidewire 10 and the steering unit 20 to increase a flexibility of the guidewire 10. However, the configuration is not limited thereto, and a configuration without the flexible polymer 43 is also possible.

In addition, although not shown in the drawings, the position display unit 23 may be provided at a surface of the guidewire steering micro-robot 4.

Referring to FIG. 5, a connector 52 of the guidewire steering micro-robot 5 may include a spring 53 at one end thereof. The spring 53 may solidify a connection between the connector 52 and the guidewire 10 and allow to adjust a flexibility of the guidewire steering micro-robot 5 by adjusting a stiffness of the spring 53.

The spring 53 may be formed in an insertable size into the connector 52. The spring 53 may be inserted into the connector 52 and may be coupled to the connector 52 by an adhesive or an interference fit method.

In addition, although not shown in the drawings, the position display unit 23 may be provided on a surface of the guidewire steering micro-robot 5.

Referring to FIG. 6, the guidewire steering micro-robot 6 may include a hollow inside of the magnetic body 21, and an end portion of a guidewire core 11 may be inserted into and connected to the hollow of the magnetic body 21. The guidewire core 11 may be shaped to have a smaller diameter toward an end portion of the guidewire core 11, but is not limited thereto.

For example, the guidewire core 11 may be formed of Nitinol or stainless steel (SUS). A nitinol may be robust against distortion and rapidly restored when it is bent due to its high elasticity. A SUS may add a power to the guidewire 10 when it moves forward due to its excellent intensity. In addition, the guidewire core 11 may use Nitinol and a SUS individually or an alloy of Nitinol and SUS that are mixed in a predetermined proportion in accordance with a purpose of a vascular procedure. However, a material of the guidewire core 11 is not limited thereto, and may be variously modified in accordance with a purpose of a vascular procedure.

In addition, the guidewire core 11 may be connected to the hollow of the magnetic body 21 by applying an adhesive thereto. Here, the magnetic body 21 is firmly constrained by the guidewire core 11. Thus, a possibility of a separation of the magnetic body 21 may be reduced.

A connector 62 may be formed in a shape of a tube or a coil. The connector 62 and the guidewire core 11 may be connected by welding or bonding.

In addition, an end portion of the magnetic body 21 inside of the connector 62 may further be provided with an internal connector 63. The internal connector 63 restricts a movement of the magnetic body 21 to prevent a possibility of a separation. However, an example is not limited thereto, and a configuration without the internal connector 63 may be possible.

In addition, although not shown in the drawings, the position display unit 23 may be provided on a surface of the guidewire steering micro-robot 6.

According to example embodiments, a position of the guidewire 10 inserted into a body may be confirmed without using a radiation by using a characteristic of the micro nanoparticle 231, that is, absorbing and emitting a light irradiated from an outside.

In addition, a side effect from a contrast medium may be removed since a position of the guidewire 10 may be confirmed without injecting a vascular contrast medium.

In addition, a direction of the guidewire 10 may be remotely controlled within a complex blood vessel structure by using an external magnetic field.

In addition, the magnetic body 21 may be used to confirm a position of the guidewire 10 with radiation imaging during a procedure as necessary.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

Accordingly, other implementations are within the scope of the following claims.

What is claimed is:

1. A guidewire steering micro-robot comprising:
   a guidewire; and
   a steering unit provided at an end portion of the guidewire, the steering unit comprising a magnetic body to control and steer a position of the guidewire by an external magnetic field, and a connector connecting the guidewire and the steering unit, the magnetic body being contained within the connector,
   wherein the steering unit further comprises a position display unit configured to absorb and emit a light irradiated from an outside of a body of a patient.

2. The guidewire steering micro-robot of claim 1, wherein the position display unit comprises a micro nanoparticle to absorb and re-emit a body transmittable light energy and a shell enclosing the micro nanoparticle.

3. The guidewire steering micro-robot of claim 2, wherein the light energy is a light energy within a shortwave infrared band.

4. The guidewire steering micro-robot of claim 1, wherein the connector is connected to the guidewire and the steering unit by heat or an adhesive.

5. The guidewire steering micro-robot of claim 1, wherein the guidewire and the steering unit are inserted into the connector.

6. The guidewire steering micro-robot of claim 5, further comprising:
   a flexible polymer between the guidewire and the steering unit.

7. The guidewire steering micro-robot of claim 6, wherein the connector comprises a hollow inside and has a shape of a coil for allowing the guidewire and the steering unit to be inserted into the connector.

8. The guidewire steering micro-robot of claim 7, wherein the coil is formed of a biocompatible metal or a polymer material.

9. The guidewire steering micro-robot of claim 1, wherein the connector further comprises a spring.

10. The guidewire steering micro-robot of claim 1, wherein the magnetic body comprises a hollow, and
    the end portion of the guidewire is inserted into and connected to the hollow of the magnetic body.

11. The guidewire steering micro-robot of claim 1, further comprising:
    a tip configured to fix a position of the magnetic body.

12. The guidewire steering micro-robot of claim 11, wherein the tip is formed of a metal or a polymer.

13. A guidewire steering micro-robot comprising:
    a guidewire; and
    a steering unit provided at an end portion of the guidewire, the steering unit comprising a magnetic body to control and steer a position of the guidewire by an external magnetic field, the steering unit further comprising a connector and a position display unit, the magnetic body being contained within the connector,
    wherein the position display unit comprises a micro nanoparticle to absorb and re-emit a body transmittable light energy and a shell enclosing the micro nanoparticle.

14. A guidewire steering micro-robot comprising:
    a guidewire; and
    a steering unit provided at an end portion of the guidewire, the steering unit comprising a magnetic body to control and steer a position of the guidewire by an external magnetic field, the steering unit further comprising a connector and a position display unit, the magnetic body being contained within the connector,
    wherein the position display unit comprises a micro nanoparticle to absorb and re-emit a body transmittable light energy and a shell enclosing the micro nanoparticle, and wherein the light energy is a light energy within a shortwave infrared band.

15. The guidewire steering micro-robot of claim 1, wherein the position display unit comprises a plurality of micro nanoparticles supported in a dispersed manner in a matrix of the connector.

\* \* \* \* \*